United States Patent
Bucina et al.

(10) Patent No.: US 11,191,528 B2
(45) Date of Patent: Dec. 7, 2021

(54) EXTERNAL HAND CONTROL FOR SURGICAL POWER TOOL

(71) Applicant: DePuy Synthes Products, Inc., Raynham, MA (US)

(72) Inventors: Stephen M. Bucina, Cocoa Beach, FL (US); James H. Kasper, Jensen Beach, FL (US); Cedric Beausse, Palm Springs, FL (US); Piotr Nowak, Jupiter, FL (US); David S. Narducci, Lake Worth, FL (US); Ovidiu Neiconi, Boynton Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/795,203

(22) Filed: Jul. 9, 2015

(65) Prior Publication Data
US 2017/0007219 A1    Jan. 12, 2017

(51) Int. Cl.
*A61B 17/00* (2006.01)
*A61B 17/16* (2006.01)

(52) U.S. Cl.
CPC .......... *A61B 17/00* (2013.01); *A61B 17/1626* (2013.01); *A61B 2017/0046* (2013.01); *A61B 2017/00199* (2013.01); *A61B 2017/00367* (2013.01); *A61B 2017/00725* (2013.01); *A61B 2017/00734* (2013.01); *A61B 2017/00982* (2013.01); *A61B 2560/045* (2013.01)

(58) Field of Classification Search
CPC .... A61B 2560/045; A61B 2017/00367; A61B 2017/0046; A61B 2017/00725; A61B 2017/00734; A61B 2017/00982; A61B 17/00; A61B 17/1626; A61B 2017/00199; A61B 2017/001199; A61B 2017/045
See application file for complete search history.

(56) References Cited

U.S. PATENT DOCUMENTS 5,196,007 A    3/1993    Ellman et al.
5,373,317 A    12/1994   Salvati et al.
(Continued)

FOREIGN PATENT DOCUMENTS

CN    2800368    7/2006
CN    102149338   8/2011
(Continued)

OTHER PUBLICATIONS

Extended European Search Report, dated Jan. 24, 2017, received in connection with European Patent Application No. 16178539.6.
(Continued)

*Primary Examiner* — Lynsey C Eiseman
*Assistant Examiner* — Jessandra F Hough
(74) *Attorney, Agent, or Firm* — Meunier Carlin & Curfman LLC

(57) ABSTRACT

A control device for a surgical power tool. The control device including a housing, an input element located on the housing, and a control unit. The housing configured to couple to a surgical power tool. The input element located proximate the top of the housing and configured to receive a user input. The control unit located within the housing, where the control unit sends user input information received at the input element to the surgical power tool.

20 Claims, 16 Drawing Sheets

(56) References Cited

U.S. PATENT DOCUMENTS

| | | | |
|---|---|---|---|
| 5,524,327 A * | 6/1996 | Mickel | F16L 3/00 24/115 A |
| 5,873,814 A | 2/1999 | Adair | |
| 6,715,078 B1 * | 3/2004 | Chasko | G06F 21/34 713/182 |
| 7,179,223 B2 | 2/2007 | Motoki et al. | |
| 7,738,971 B2 | 6/2010 | Swayze et al. | |
| 7,846,150 B2 | 12/2010 | Hamel et al. | |
| 7,883,458 B2 | 2/2011 | Hamel | |
| 8,746,530 B2 | 6/2014 | Giordano et al. | |
| 8,840,603 B2 | 9/2014 | Shelton et al. | |
| 9,023,071 B2 | 5/2015 | Miller et al. | |
| 9,757,101 B2 | 9/2017 | Regere et al. | |
| 10,076,340 B2 | 9/2018 | Belagali et al. | |
| 10,149,711 B2 | 12/2018 | Bittenson | |
| 10,456,010 B2 | 10/2019 | Sholev | |
| 10,517,682 B2 | 12/2019 | Giordano et al. | |
| 10,588,629 B2 | 3/2020 | Malinouskas et al. | |
| 10,993,717 B2 | 5/2021 | Shelton et al. | |
| 11,000,277 B2 | 5/2021 | Giordano et al. | |
| 2003/0048598 A1 * | 3/2003 | Lee | G06F 1/1626 361/679.55 |
| 2004/0180703 A1 * | 9/2004 | Kim | H04N 1/2112 455/575.1 |
| 2005/0004559 A1 | 1/2005 | Quick et al. | |
| 2005/0020909 A1 * | 1/2005 | Moctezuma de la Barrera | A61B 17/62 600/424 |
| 2005/0078817 A1 * | 4/2005 | Lee | H04M 1/0237 379/433.12 |
| 2006/0068834 A1 | 3/2006 | Jones | |
| 2007/0117425 A1 * | 5/2007 | Wang | H05K 3/325 439/135 |
| 2008/0077158 A1 | 3/2008 | Haider et al. | |
| 2008/0188870 A1 | 8/2008 | Andre et al. | |
| 2009/0253472 A1 | 10/2009 | Kim | |
| 2009/0256817 A1 * | 10/2009 | Perlin | G06F 3/0233 345/174 |
| 2012/0203213 A1 * | 8/2012 | Kimball | A61B 17/320068 606/1 |
| 2012/0283707 A1 | 11/2012 | Giordano et al. | |
| 2013/0307529 A1 | 11/2013 | Baumgartner | |
| 2014/0039382 A1 * | 2/2014 | Fern | A61B 5/14532 604/65 |
| 2015/0083772 A1 | 3/2015 | Miller et al. | |
| 2015/0182230 A1 * | 7/2015 | Belagali | A61B 17/14 606/82 |
| 2015/0272557 A1 * | 10/2015 | Overmyer | G05B 19/05 606/1 |
| 2015/0272579 A1 * | 10/2015 | Leimbach | A61B 17/07207 227/178.1 |
| 2015/0301601 A1 | 10/2015 | Ibach et al. | |
| 2017/0007219 A1 | 1/2017 | Bucina et al. | |
| 2017/0086834 A1 | 3/2017 | Auld et al. | |
| 2018/0049794 A1 | 2/2018 | Swayze et al. | |
| 2018/0049795 A1 | 2/2018 | Swayze et al. | |
| 2018/0199949 A1 | 7/2018 | Chien et al. | |
| 2019/0059968 A1 | 2/2019 | Bittenson | |
| 2019/0201139 A1 | 7/2019 | Shelton et al. | |
| 2019/0217460 A1 | 7/2019 | Mahalingappa et al. | |
| 2020/0375681 A1 | 12/2020 | Cummings-Kralik et al. | |
| 2020/0405404 A1 | 12/2020 | Shelton et al. | |

FOREIGN PATENT DOCUMENTS

| | | |
|---|---|---|
| CN | 102198014 | 9/2011 |
| CN | 202419252 | 9/2012 |
| EP | 2245981 B1 | 9/2018 |
| EP | 3506281 A1 | 7/2019 |
| EP | 3132757 B1 | 7/2020 |
| EP | 3687024 A1 | 7/2020 |
| EP | 2852336 B1 | 6/2021 |
| JP | 2000-254136 | 9/2000 |
| JP | 2013-192952 | 9/2013 |
| RU | 2664168 C2 | 8/2018 |
| WO | 2019162761 A1 | 8/2019 |
| WO | 2019173574 A1 | 9/2019 |
| WO | 2020051443 A1 | 3/2020 |

OTHER PUBLICATIONS

Search Report, dated Mar. 24, 2020, received in connection with CN Patent Application No. 201610537623.1 (English translation).

Supplementary Search Report, dated Nov. 9, 2020, received in connection with corresponding CN Patent Application No. 201610537623.1 (English translation).

* cited by examiner

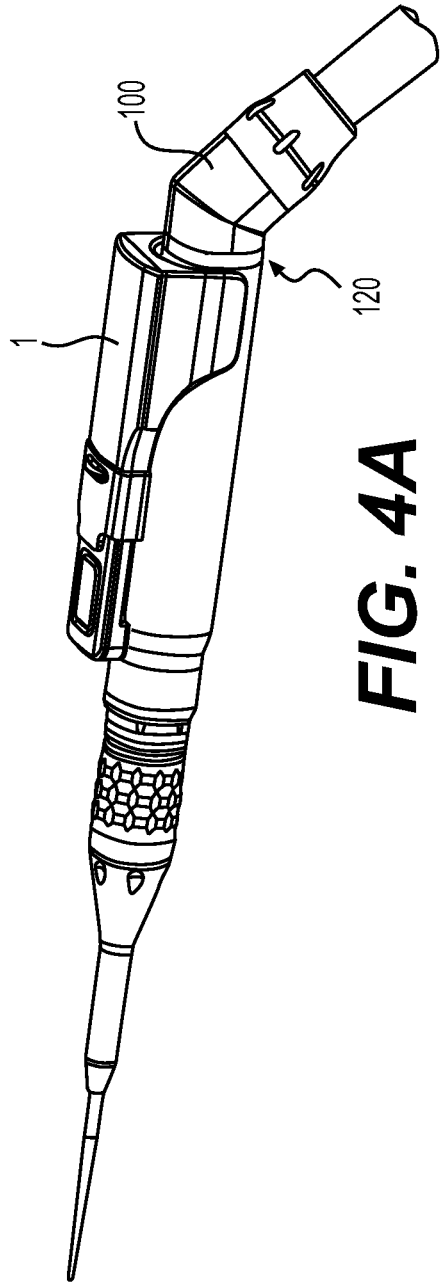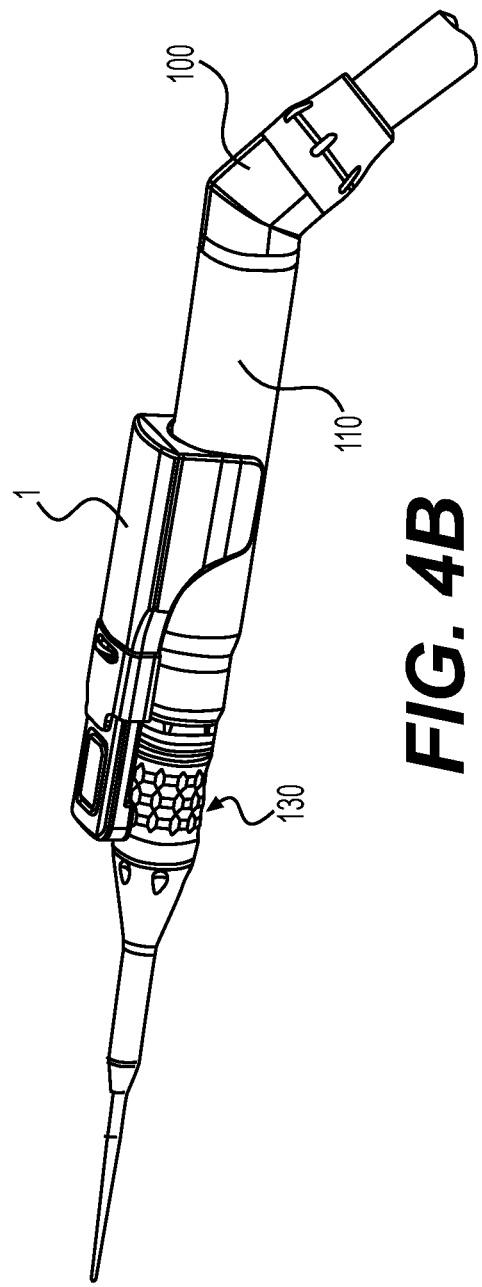
FIG. 4A
FIG. 4B

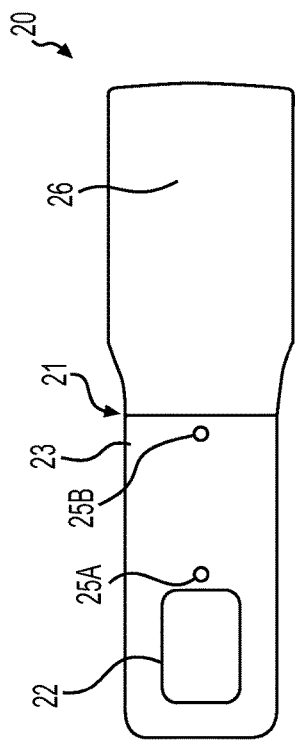 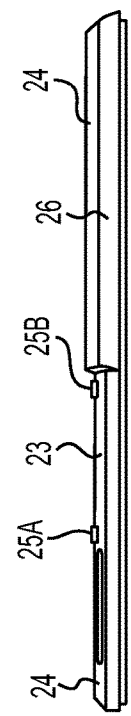 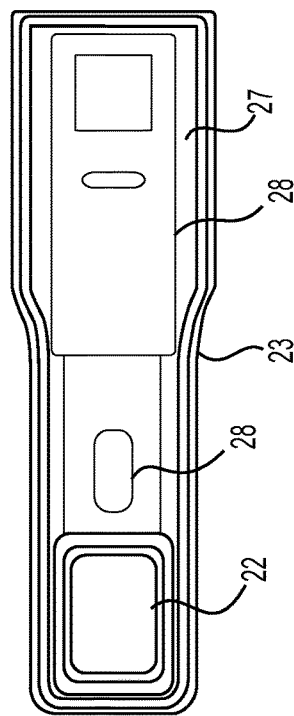
*FIG. 7C*  *FIG. 7D*  *FIG. 7E*

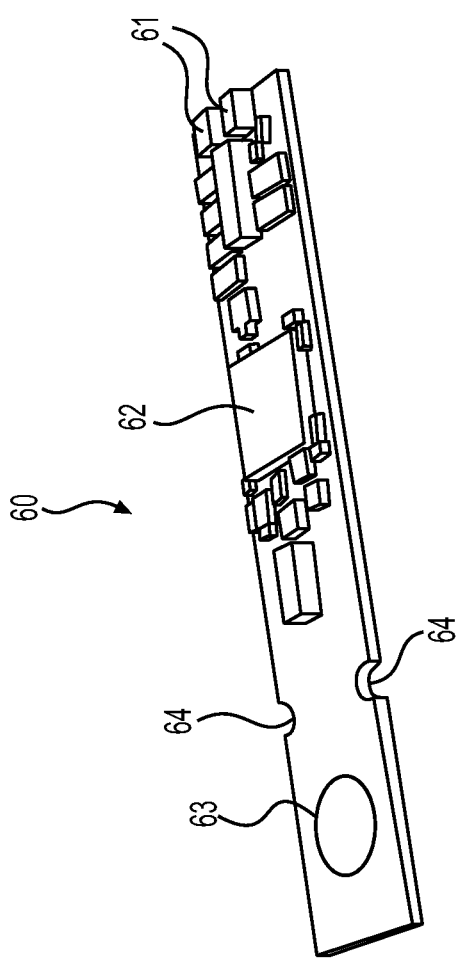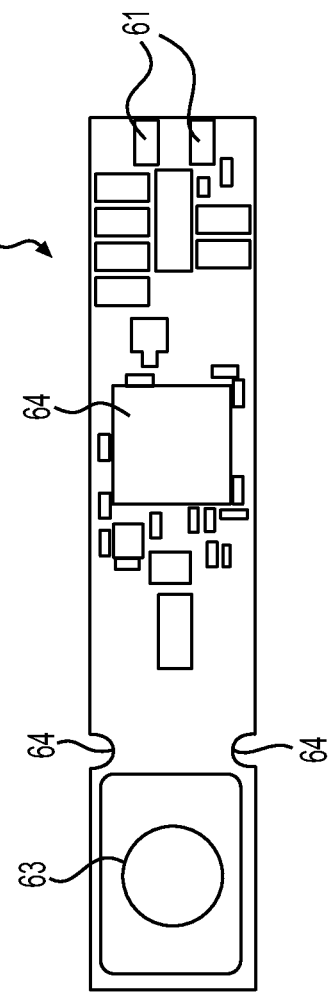
FIG. 10A
FIG. 10B

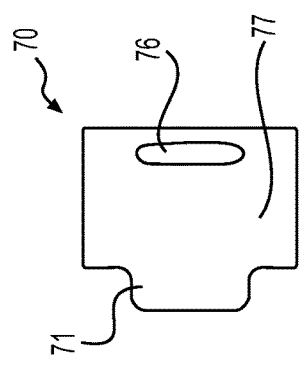
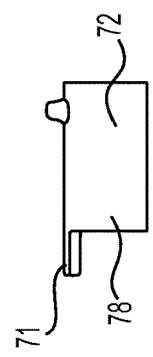
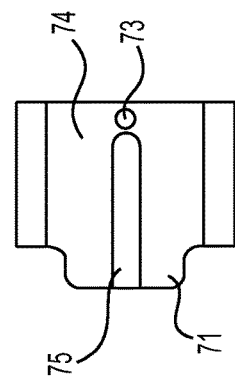
FIG. 11C
FIG. 11D
FIG. 11E
FIG. 11F

EXTERNAL HAND CONTROL FOR SURGICAL POWER TOOL

TECHNICAL FIELD

This disclosure relates to a device for the controlled operation of a surgical power tool, and more particularly to a wireless control device mounted to the handpiece of the power tool.

BACKGROUND

Many surgical procedures require the use of electrically or pneumatically powered tools, such as burrs and saws. Typically, operation of a surgical power tool is controlled either by a foot pedal or a hand control/input (e.g., a pushbutton, switch, or lever located on the handpiece of the tool). A common drawback of a foot pedal controller is the lack of mobility in the operating room. Many surgical suites are crowded with medical equipment and hospital staff, making the physician's movement around the patient (and relocation of the foot pedal) complicated and time consuming A system utilizing a controller located along the handpiece of the power tool can cause problems of visibility of control of the power tool. For example, depending on the surgical procedure, patient anatomy, and surgeon's hand size and grip position, visibility of the surgical site and control of the power tool can be limited/compromised by the surgeon's hand or the controller itself. Accordingly, there remains a need in the art to provide a safe and effective apparatus and method for ensuring visibility of a surgical site and superior physician control of a hand-operated power tool.

SUMMARY

Presented are systems and methods for providing a control device for a surgical power tool. The control device can include a housing, an input element located on the housing, and a control unit. The housing can be sized and configured to be coupled to a surgical power tool. The input element can be located proximate the top of the housing for receiving a user input. The control unit can be located within the housing, where the control unit sends user input information received at the input element to the surgical power tool.

Another aspect of the present disclosure is directed to a surgical power tool and an associated control device. The control device can be coupled to the surgical power tool, the control device can be moved along or around the handpiece of the surgical power tool. The control device can include a housing, a pressure responsive touch pad, and a control unit. The housing can include arms for coupling the control device to the power tool. The arms can extend from the housing and can engage at least a portion of the outer perimeter of the handpiece of the power tool. The pressure responsive touch pad can be located on a top surface of the control device and can receive a user input. The control unit can send user input information received at the input element to the power tool for directing a speed of the power tool or other functions.

A further aspect of the present disclosure is directed to a method of controlling a surgical power tool using a control unit movable and releasably coupled to the handpiece of a surgical power tool. The control device can be first oriented with respect to the handpiece such that the opening between arms extending from the bottom surface of the control device is positioned over the handpiece. The control device can then be pressed onto the handpiece as the arms flex/expand to advance over and/or around the handpiece. Once coupled to the handpiece, the control device can be moved by the surgeon along the body of the handpiece. The surgeon can slide and/or rotate the control device along/around the handpiece. The surgeon can then activate the power tool by providing pressure at the input surface. By varying the pressure at the input surface, the input information can be varied resulting in a corresponding change in the operation of the power tool.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

The device is explained in greater detail in the following drawings. The drawings are merely exemplary to illustrate the structure of preferred devices and certain features that may be used singularly or in combination with other features. The invention should not be limited to the examples shown.

FIGS. 4A-4B are perspectives views of an example control device coupled to a surgical power tool;

FIG. 7C is a top view of the top housing cover of FIG. 7A;

FIG. 7D is a side view of the top housing cover of FIG. 7A;

FIG. 7E is a bottom view of the top housing cover of FIG. 7A;

FIG. 10A is a perspective view of an example control unit;

FIG. 10B is a top view of the example control unit of FIG. 10A;

FIG. 11C is a top view of the example slide cover of FIG. 11A;

FIG. 11D is a side view of the example slide cover of FIG. 11A;

FIG. 11E is a bottom view of the example slide cover of FIG. 11A;

FIG. 11F is an end view of the example slide cover of FIG. 11A;

Like reference symbols in the various drawings indicate like elements.

DETAILED DESCRIPTION

Figure 1:
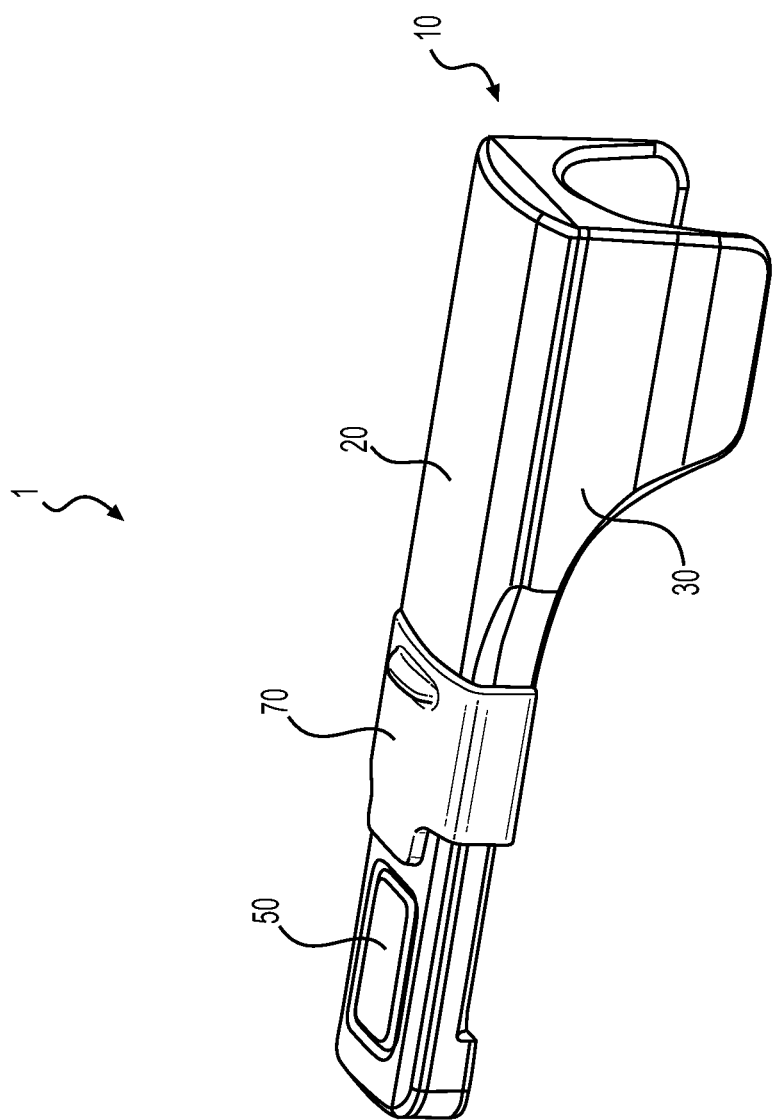
FIGS. 1-2 are perspective views of an example control device.

Certain terminology is used in the following description for convenience only and is not limiting. The words "right," "left," "lower," and "upper" designate direction in the drawings to which reference is made. The words "inner" and "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The terminology includes the above-listed words, derivatives thereof, and words of similar import.

Figure 2:
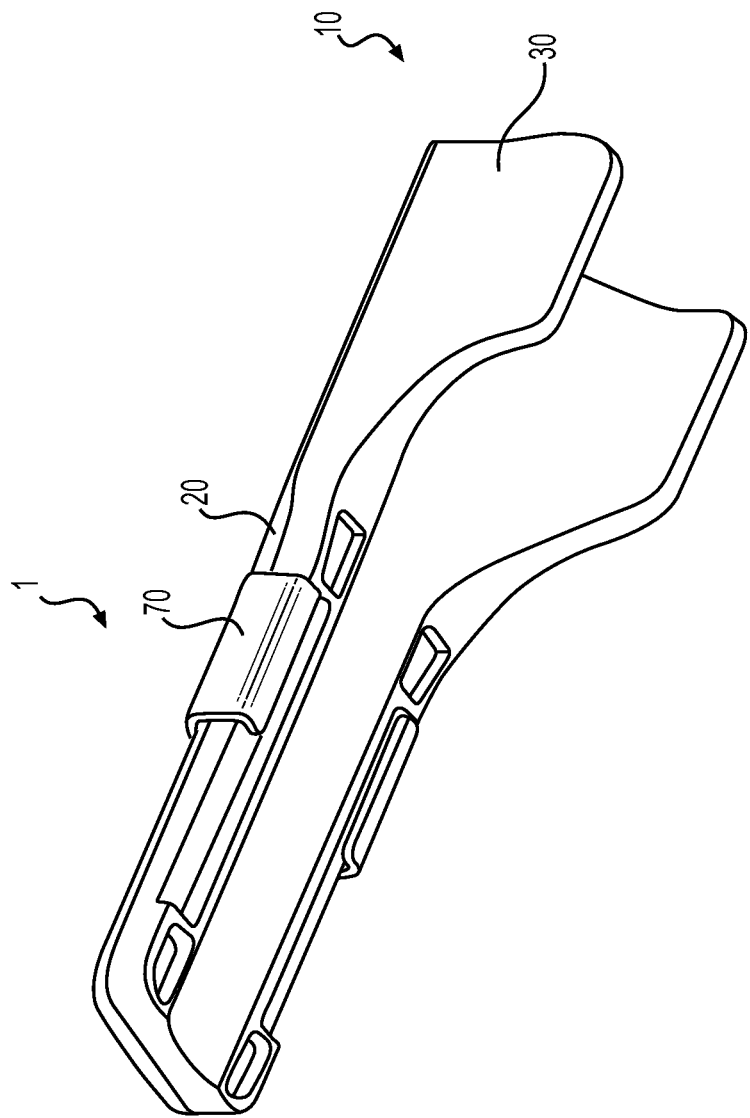

Certain examples of the invention will now be described with reference to the drawings. In general, such embodiments relate to a control device movably and releasably coupled to the handpiece of a surgical power tool for use in controlling the operation of the power tool. FIG. 1 provides a top perspective view of an example control device 1. The control device 1 can include a housing 10, an input element 50, and a control unit 60 (not shown). The housing 10 is sized and configured for coupling the control device 1 to a surgical power tool 100. As will be explained in more detail below, the housing 10 can include various engagement features that allow the housing 10/control device 1 to be releasably and/or moveably coupled to the power tool 100. For example, as illustrated in FIG. 2, the bottom surface of the housing 10 can have a shape complementary to the outer surface of the power tool 100. Additionally, the housing 10 can include arms 32 for securing the housing 10 to the power tool 100.

Figure 3:
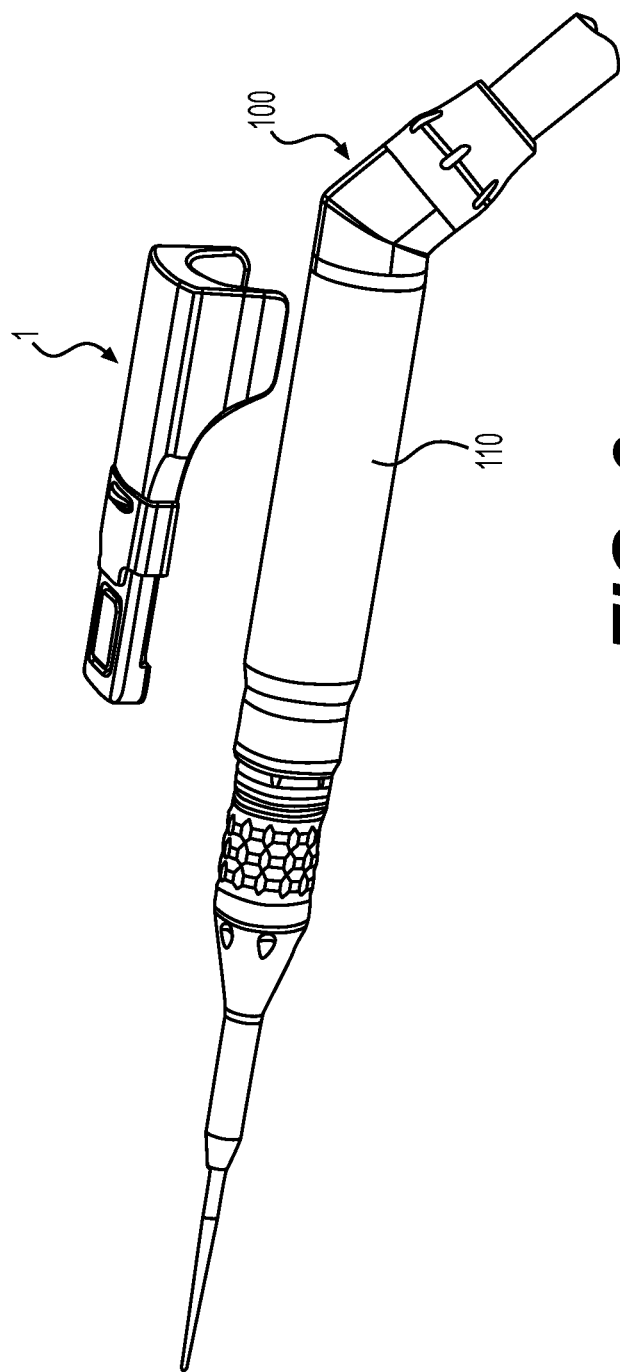
FIG. 3 is a perspective view of an example control device and surgical power tool.

FIG. 3 illustrates the control device 1 aligned with the handpiece 110 of an example surgical power tool 100. It is contemplated that the example power tool 100 can include any number of power tools typically used in a surgical procedure. The power tool 100 can be used in any number of surgical procedures in orthopaedics, traumatology, neurosurgery, neurotology, spinal procedures, otolaryngology, cranio-facial surgery, etc. Example power tools 100 include, for example, drills, saws, shavers, drivers, reamers, pinners, staplers, microdebriders, etc. For example, the Anspach XMax® series or the E-Max® series, pneumatic and electric power tools, respectively, are contemplated for use with the disclosed control device and are commercially available from DePuy Synthes Products, Inc. of Raynham, Mass.

The power tool 100 can be electrically (wired or wireless) and/or pneumatically powered. As will be explained in more detail below, the housing 10 of the control device 1 can be coupled to the handpiece 110 of the power tool 100. Depending on the surgical procedure, patient anatomy, and surgeon grip position and visibility, the surgeon may wish to position the control device 1 at various locations along and/or around the handpiece 110 of the power tool 100. For example, as different length attachments (e.g., burrs, blades) are attached to the handpiece 110, the distance between the surgical site/working area and the surgeon's grip position on the control device 1/handpiece 110 increases, making control more difficult. The surgeon may wish to position the control device 1 forward on the handpiece, closer to the surgical site/working area, thereby giving the surgeon more control and stability over the power tool 100/handpiece 110. Accordingly, it is contemplated that the control device 1 can be positioned at any location along the handpiece 110. For example, as illustrated in FIG. 4A, the control device 1 can be located rearward on the handpiece 110, proximate the control end 120 of the power tool 100. As illustrated in FIG. 4B, the control device 1 can be located forward on the handpiece 110, proximate the operating end 130 of the power tool 100.

Figure 5:
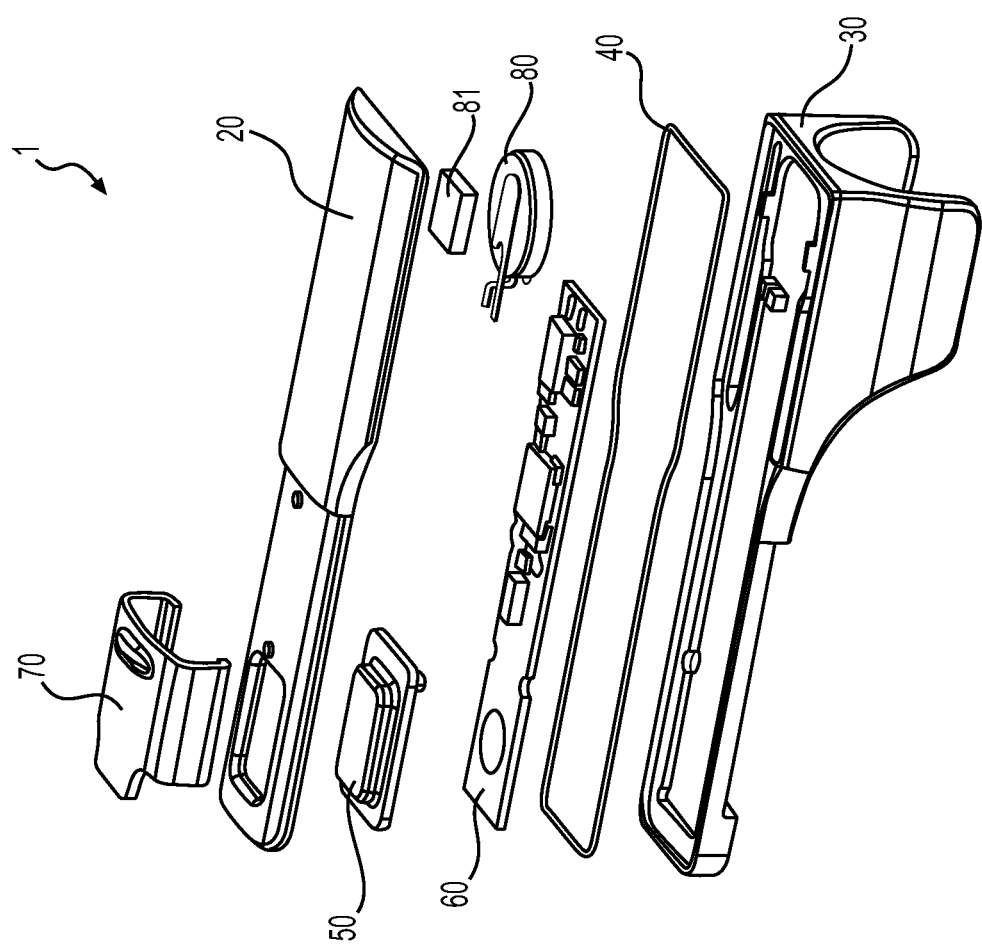
FIG. 5 is an exploded view of the example control device of FIG. 1.
Figure 6:
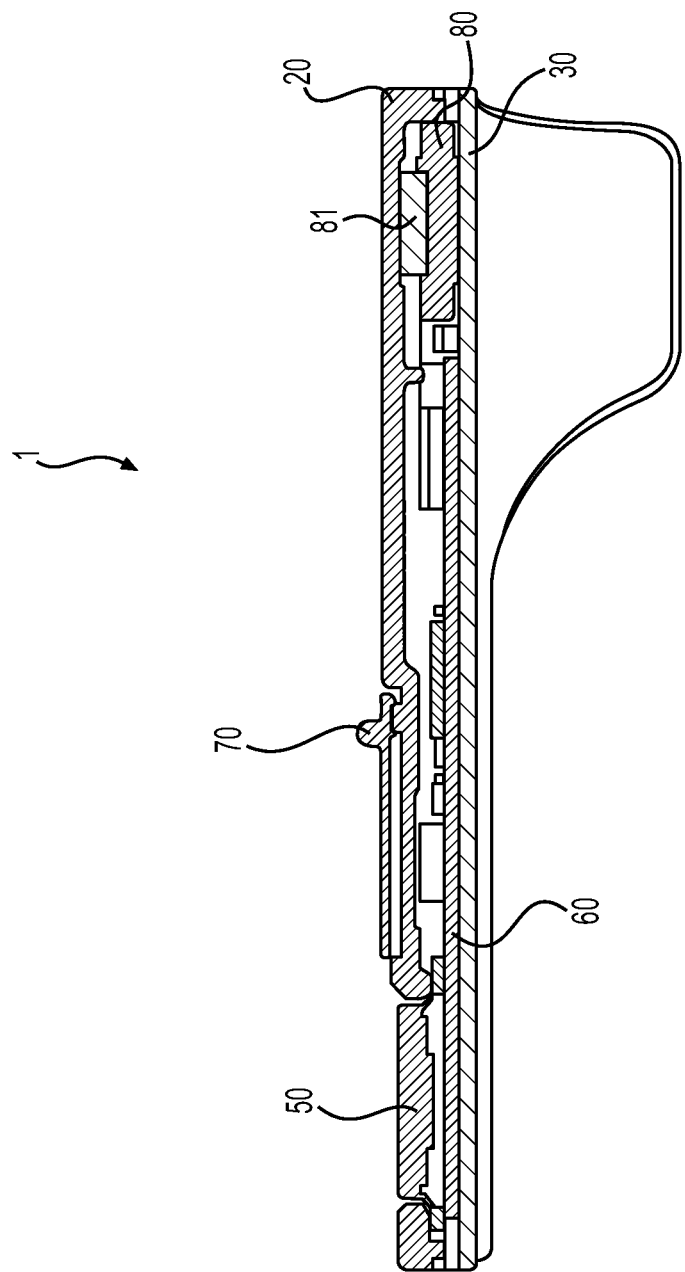
FIG. 6 is a section view of the example control device of FIG. 1.

FIG. 5 provides an exploded view of the various components of an example control device 1. FIG. 6 provides a cross-section view of the example control device 1 illustrated in FIG. 1. The control device 1 can include a housing 10, an input element 50, a control unit 60, and a slide cover 70 movable along the housing 10. As illustrated in FIGS. 5 and 6, the housing 10 can include a top housing 20 and a bottom housing 30. The top housing 20 and the bottom housing 30 can be permanently or releasably coupled together. The top housing 20 and the bottom housing 30 can be coupled using screws, hooks, clips, welds, or any other form of mechanical fastener known in the art. It is also contemplated that the top housing 20 and the bottom housing 30 can be coupled using a chemical fastener/adhesive. For example, as illustrated in FIG. 5, the top housing and the bottom housing 30 can be coupled using a pressure-sensitive adhesive 40 or an epoxy. It is contemplated that the top housing 20 and the bottom housing 30 can be formed as a single, integral housing.

FIGS. 7A-7E provide various views of an example top housing 20. The top housing 20 can include an elongated body portion 21 sized and configured to extend along a length of the handpiece 110 of the surgical power tool 100. The top housing 20 can include an opening 22 providing access to the input element 50. As will be explained in more detail below, the opening 22 can be located proximate an input position (input element contacts 63) on the control unit 60 such that user input information received at the input element 50 is transferred/received by the control unit 60. The top housing 20 can also include a recessed surface 23 sized and configured to accommodate movement of the slide cover 70. The top housing 20 can also an engagement feature for fixing the position of the slide cover 70. For example, the top surface 24 of the top housing 20 can include protrusions 25 for engaging a corresponding recess 73 provided in the slide cover 70. The first protrusion 25A can secure the slide cover 70 is a first, non-operating, position where the slide cover 70 covers over at least a portion of the input element 50 and prevents accidental activation of the power tool 100. The second protrusion 25B can be used to secure the slide cover 70 in a second, operating, position away from the input element 50, illustrated, for example, in FIG. 1.

Figure 7B:
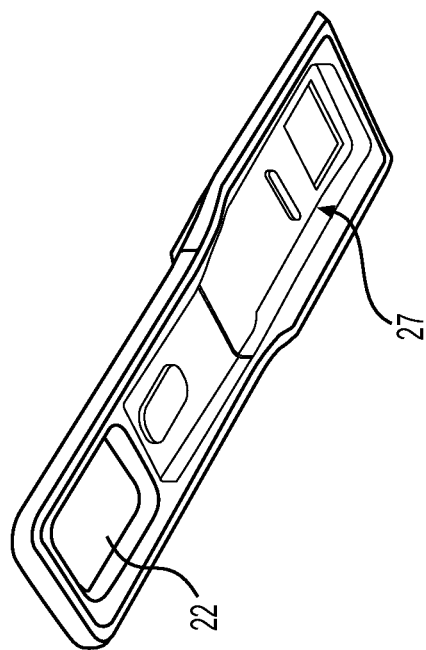
FIGS. 7A-7B are perspective views of an example top housing cover.
Figure 7A:
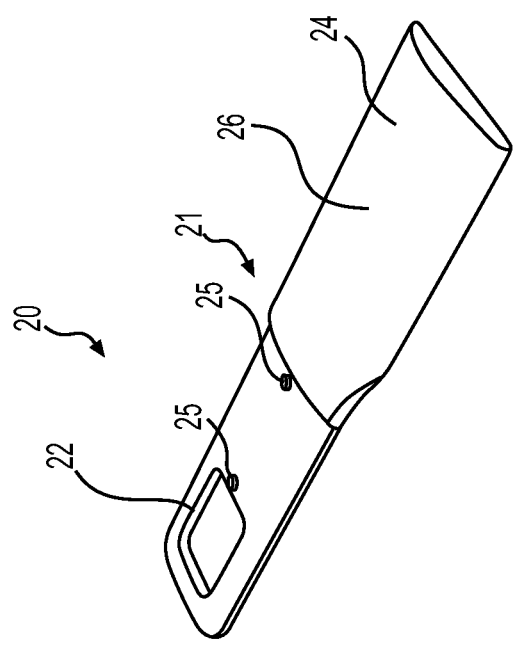

The top housing 20 can include an outer grip surface 26 to accommodate a secure grip by the surgeon during the use, illustrated in FIGS. 7A, 7C, and 7D. The grip surface 26 can include a contoured outer surface and/or textured surface features to enhance grip/purchase between the surgeon's hand and the control device 1. The inside surface 27 of the top housing 20 can include recessed portions 28 as illustrated in FIGS. 7B and 7E. These recessed portions 28 can be sized and configured to accommodate the input element 50 and control unit 60 components.

FIGS. 8A-8F provide various views of an example bottom housing 30. The bottom housing 30 can include an elongated body portion 31 sized and configured to extend along a length of the handpiece 110 of the surgical power tool 100. The bottom housing 30 can include an engagement feature for coupling the bottom housing 30 to the handpiece 110. The bottom housing 30 can be permanently or releasably coupled to the handpiece 110. The engagement features can be provided such that the bottom housing 30 is moveably coupled along the handpiece 110. For example, the bottom housing 30 may slide along and/or rotate around the handpiece 110. The surgeon may couple the housing 10/bottom housing 30 to the handpiece 110 and wish to relocate along the body of the handpiece 110 before/during/after the surgical procedure. In which case, the housing 10/bottom housing 30 may slide along the body of the handpiece 110 to the desired position. The housing 10/bottom housing 30 may also be fixed to the power tool 100 such that it does not side along/rotate with respect to the body of the handpiece 110.

The engagement features included on the bottom housing 30 can include arms 32 extending in a direction away from bottom surface 33 of the housing 10/bottom housing 30 and around/towards the handpiece 110 of the power tool 100. As illustrated in FIGS. 4A and 4B, the arms 32 can be configured to engage at least a portion of the outer perimeter of the handpiece 110. It is contemplated that the arms 32 can be sized and configured to engage a portion of the power tool 100 other than the handpiece 110. The arms 32 can engage the outer perimeter of the handpiece 110/power tool 100 by a snap fit, press fit, a weld, or any other mechanical or chemical fastener known in the art.

Figure 8B:
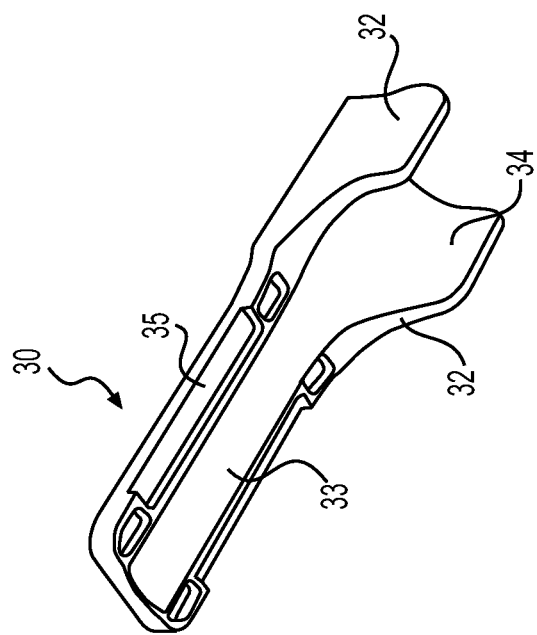
FIGS. 8A-8B are perspective views of an example bottom housing cover.

The arms 32 can include an inside surface 34 having a shape corresponding to the shape of the handpiece 110/power tool. As illustrated in FIGS. 8B, 8E and 8F, the inside surface 34 defines a round surface corresponding to the outside perimeter of the handpiece 110. Likewise, the bottom housing 30 can include a bottom surface 33 having a shape corresponding to the shape of the handpiece 110/power tool 100. For example, as illustrated in FIGS. 8B and 8F, the bottom surface 33 has a rounded shaped corresponding to the cylindrical shape of the handpiece 110.

The bottom housing 30 can include recessed surfaces 35 sized and configured to accommodate movement of the slide cover 70. For example, as illustrated in FIGS. 2, 8A, 8B, 8D and 8E the bottom surface 33 of the bottom housing 30 can include recessed surfaces 35 extending along the left and right side of the body portion 31 of the bottom housing 30. The recessed surfaces 35 provide a groove/slot for the arms 72 of the slide cover 70. The recessed surfaces 35 can extend along the entire length of the bottom housing 30. Alternatively, as illustrated in FIGS. 8D and 8E, the recessed surfaces 35 can extend along only a portion of the length of the bottom housing 30 and the ends of the recessed surfaces 35 act as stops for the slide cover 70. That is, movement of the recessed cover between a first position and a second position is limited by contact between the arms 72 and the ends of the recessed surfaces 35.

Figure 8A:
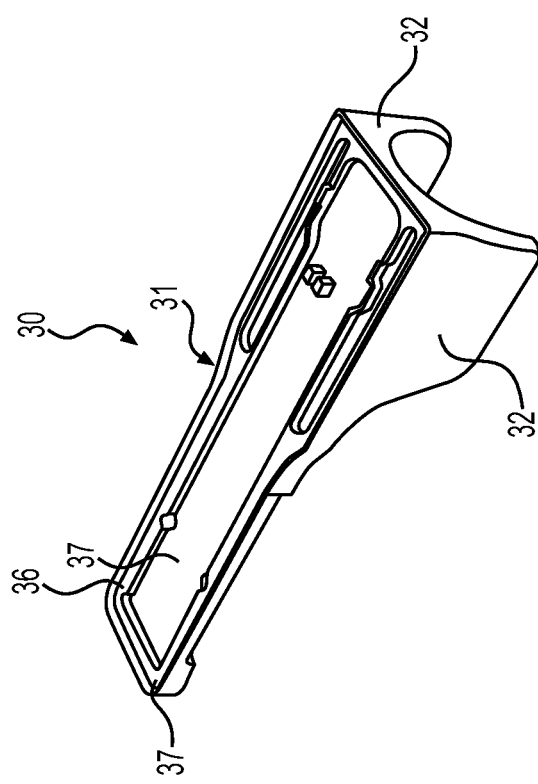
Figure 8C:
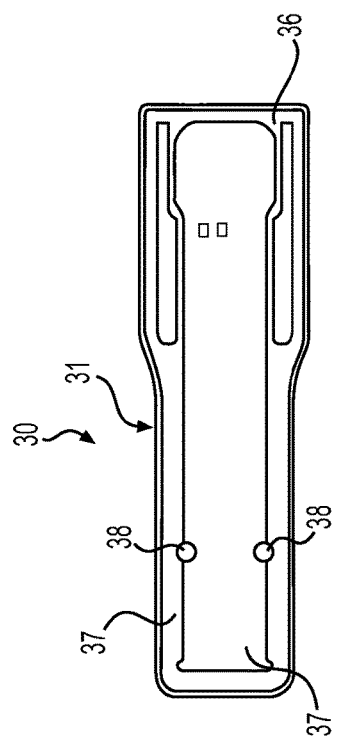
FIG. 8C is a top view of the bottom housing cover of FIG. 8A.
Figure 8D:
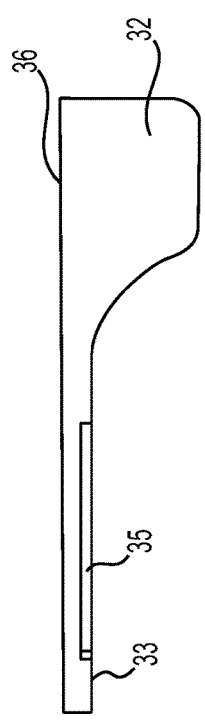
FIG. 8D is a side view of the bottom housing cover of FIG. 8A.
Figure 8E:
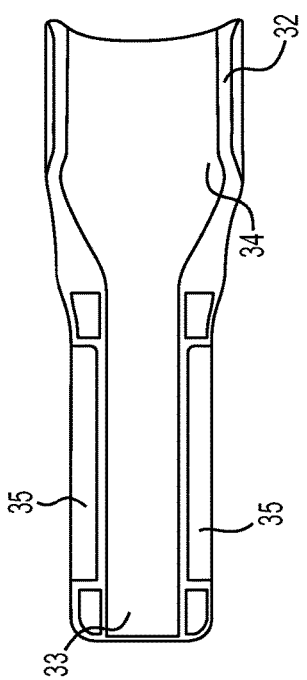
FIG. 8E is a bottom view of the bottom housing cover of FIG. 8A.
Figure 8F:
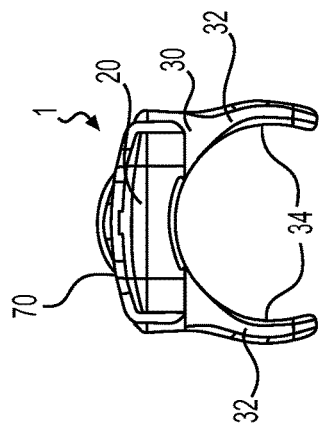
FIG. 8F is an end view of the bottom housing cover of FIG. 8A.

The top surface 36 of the bottom housing 30 can include recessed portions 37 as illustrated in FIGS. 8A and 8C. These recessed portions 37 can be sized and configured to accommodate the input element 50 and the control unit 60.

The inside surface 36 can also include an anchor point 38 for coupling the bottom housing 30 to the input element 50. For example, as illustrated in FIGS. 8A and 8C, the bottom housing 30 can include two circular-shaped cavities 38 for receiving a similarly-shaped anchors 54 extending from the input element 50. The anchors 54 of the input element 50 can be permanently and/or releasably coupled to the bottom housing 30. The anchors 54 can be press fit, snap fit, welded, or coupled to the bottom housing 30 using any other mechanical or chemical fastener known in the art.

FIGS. 9A-9F provide various views of an example input element 50. The input element 50 can include a pressure responsive touch pad for receiving the surgeon's input. As will be explained in more detail below, the input element 50 can facilitate an electrical and/or mechanical connection that translates a user input at the input surface 51 to the control unit 60, thereby controlling operation of the surgical power tool 100.

Figure 9B:
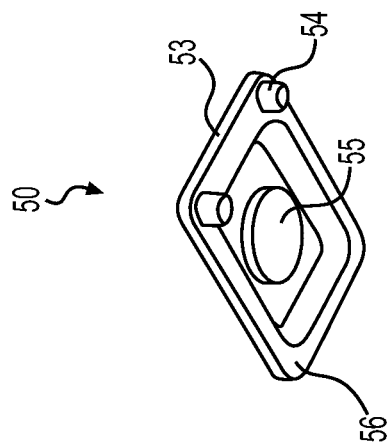
FIGS. 9A-9B are perspective views of an example input element.
Figure 9A:
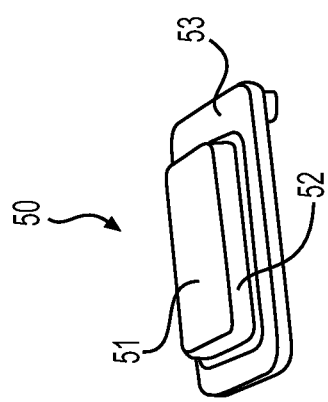
Figure 9F:
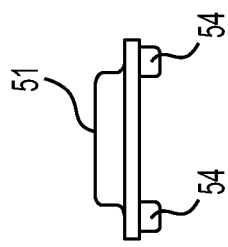
FIG. 9F is an end view of the example input element of FIG. 9A.
Figure 9C:
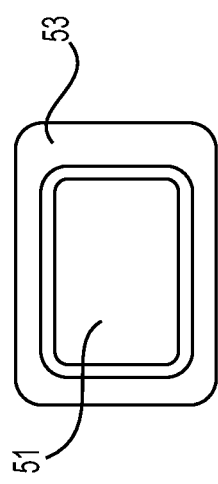
FIG. 9C is a top view of the example input element of FIG. 9A.

The input surface 51 can be located at the top surface 24 of the top housing 10. The input surface 51 can be accessible via the opening 22 provided in the top housing 10. For example, as illustrated in FIGS. 1, 5, and 6, the input element 50 can extend from inside the housing 10 and partially into and/or through the opening 22 provided in the top housing 20. In an example control device 1, the input surface 51 is recessed below the top surface 24 of the top housing 20. The input surface 51 can have a shape corresponding to the shape of the opening 22. As illustrated in FIGS. 7C and 9C, the input surface 51 and the opening 22 can define rectangular shape. It is contemplated that the input surface 51 and/or the opening 22 can define can define any suitable shape including, for example, circular, elliptical, square, rectangular, or any other regular or irregular shape.

Figure 9D:
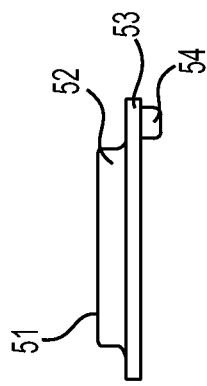
FIG. 9D is a side view of the example input element of FIG. 9A.
Figure 9E:
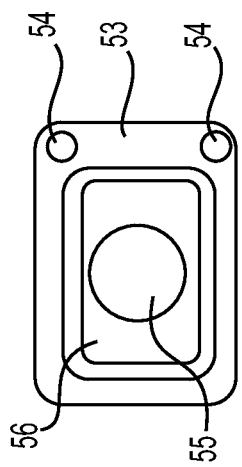
FIG. 9E is a bottom view of the example input element of FIG. 9A.

As outlined above, the input element 50 can include a pressure responsive touch pad. The input element 50 can be constructed from a flexible/compliant material. For example the input element 50 can be constructed from silicone rubber any other flexible/compliant material known in the art. In an example control device 1, the input element 50 can be constructed having uniform flexibility/elasticity. In another example, various portions of the input element 50 can have differing flexibility/elasticity. As illustrated in FIGS. 9A and 9D, the input surface 51 can extend in a direction parallel to the base portion of the input element 50. The input element 50 can include flexible side walls 52 that extend between the input surface 51 and the base portion 53. The flexible side walls 52 can be provided such that pressure on the input surface 51 can result in translational movement of the input surface 51 with respect to the base portion 53. The side walls 52 can have increased flexibility with respect to the input surface 51 and/or the base portion 53.

The input element 50 can be permanently or releasably coupled to the housing 10. In another example (not shown), the input element 50 can be integrally formed with the housing 10. As described above, and as illustrated in FIGS. 9B and 9D, the input element 50 can include anchors 54 sized and configured for coupling the input element 50 to the housing 10. The anchors 54 can extend from the base portion 53 in a direction away from the input surface 51. The input element 50 can include any number of anchors 54 suitable for coupling the input element 50 to the housing 10. When assembled, the anchors 54 can extend through opening 64 provided in the control unit 60 before coupling to the housing 10.

FIGS. 10A and 10B provide a perspective and plan view of an example control unit 60. The control unit 60 can be located within the housing 10 and can be used to send user input information received at the input element 50 to the surgical power tool 100 to direct operation of the power tool 100. For example, the control unit 60 can provide a wired or wireless communication link with the corresponding control unit of the power tool 100. The control unit 60 can include a PCB (printed circuit board), a flexible circuit or any other circuitry for electrically connecting the electronic components of the control unit 60 and providing two-way communication between the control unit 60 and the power tool 100. The control unit 60 can facilitate two-way communication between the control device 1 and the power tool 100, i.e., the control unit 60 be used to communicate input information received at the input element 50 to surgical power tool 100 and also receive operation information from the power tool 100.

Components of the control unit 60 can include battery contacts 61, a wireless communication unit 62 (e.g., radio chip antenna, microcontroller with integrated radio, etc.) for communicating with the power tool, and input element contacts 63, an analog-to-digital converter for converting the user's input into an electrical signal for wireless transmission to the power tool, etc. A battery 80 can be positioned in-line with the control unit 60. As illustrated in FIGS. 7E and 8C, the top housing 20 and the bottom housing 30 can include recessed portions 28 and 27 sized and configured to receive the battery to ensure the low profile design of the housing 10. A compressive pad 81 may be included within the housing 10 to secure the position of the battery 80 against contacts 61 provided on the control unit 60.

The input element 50 can be located within the control device 1/housing 10 at a position proximate the control unit 60 such that a user input at the input surface 51 activates the input element contacts 63 on the control unit 60. In an example control device 1, the input element 50 can include a carbon or gold pill 55 placed on the bottom surface 56 of the input element 50 proximate the contacts 63. The carbon pill 55 can be provided within the input element 50 by means of a silicone overmold (or other insulative material). Upon depression of the input element 50, the pill 55 comes into contact with the control unit contacts 63 and completes an electrical connection. As pressure is removed from the input surface 51, the electrical connection ends and the input element 50 and pill 55 return to their neutral position. The force to operate (actuation force) the input element 50 is approximately 100 g (+/−25 g).

Varying the user input provided at the input surface 51 can vary the input information received at/measured by the control unit 60. That is, varying the input information can result in a corresponding change in power tool 100 operation. For example, it is contemplated that the control device 1 can be used to control the on/off function, speed, torque, direction, illumination, irrigation, suction, or any other function completed by a surgical power tool. In one example, the increased pressure/force applied at the input surface 51 can correspond to an increased power tool 100 speed, torque, etc. Likewise, varying the location and/or direction of the user input on the input surface 51 can result in a corresponding change in input information and power tool 100 operation. For example, applying input force at a certain location on the input surface 51 can be used to provide a specific operation instructions to the power tool 100 (e.g., on/off, speed, torque, direction). Likewise, sweeping/moving the finger across the input surface 51 can also be used to provide a specific instruction to the power tool 100 (e.g., on/off, speed, torque, direction).

FIGS. 11A-11F provide various views of an example slide cover 70. The slide cover 70 is movable along the housing 10 (top housing 20 and bottom housing 30) between a first, non-operating, position where the slide cover 70 covers over at least a portion of the input element 50 and a second, operating, position allowing access to the input element 50. The second, operating, position is illustrated in FIG. 1. The slide cover 70 can include an extension 71 provided at the distal end of the slide cover 70 for extending over/covering the input surface 51 of the input element 50 when the slide cover 70 is in (or proximate) the first, non-operating, position.

The slide cover 70 can also include two downwardly extending arms 72 that wrap around the side edge of the housing 10 (top housing 20 and bottom housing 30). The arms 72 can extend around at last a portion of the side and bottom surfaces of the housing 10 to engage the recessed surfaces 35 provided on the bottom surface 33 of the housing 10/bottom housing 30. The arms 72 can move along the recessed surfaces 35 between a first and second position. The ends of the recessed surfaces 35 can act as a stop for the slide cover 70.

Figure 11B:
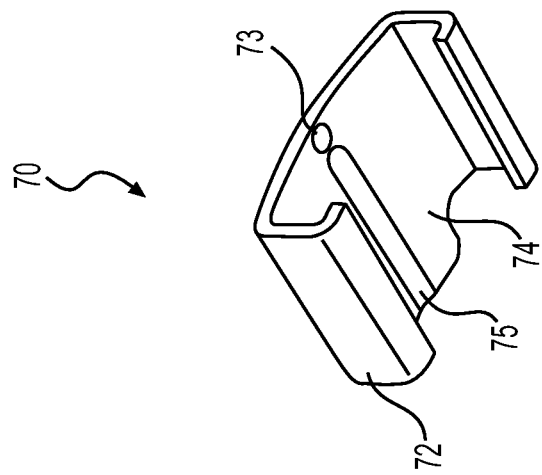
FIGS. 11A-11B are perspective views of an example slide cover.

The slide cover 70 can include an engagement feature for fixing the position of the slide cover 70 along the housing 10/top housing 20. For example, as illustrated in FIGS. 11B and 11E, the slide cover 70 can include recesses 73 on its bottom surface 74 for engaging a corresponding protrusion 25 provided in the top housing 20. The bottom surface 74 can also include an elongated channel 75 terminating proximate the circular-shaped recess 73. It is contemplated that the engagement features, recess 73 and elongated channel 75, can have any suitable shape/profile corresponding to the protrusion 25. The recess 73 and elongated channel 75 can have a circular, elliptical, square, rectangular, or any other regular or irregular shape. As the slide cover 70 moves along the housing 10, the protrusions 25 provided in the top housing 20 move along the channel 75 of the slide cover 70. Once moved to the first or second position, the corresponding housing protrusion 25 engages the recess 73 provided in the slide cover 70. The surgeon can disengage the engagement features (protrusion/recess) using hand force.

Figure 11A:
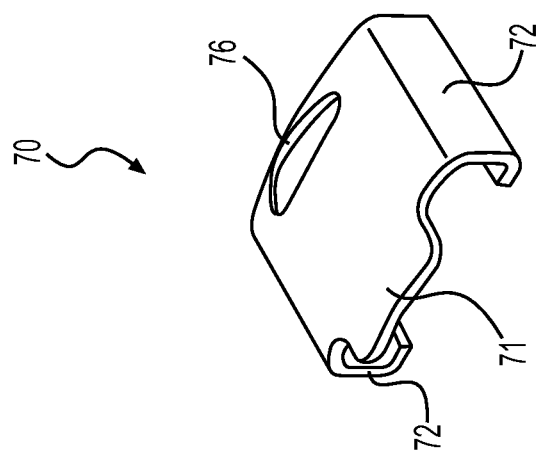

The slide cover 70 can include a grip surface 76 to accommodate a secure grip and provide a leverage point to facilitate movement of the slide cover 70 by the surgeon. As illustrated in FIGS. 11A, 11C, 11D, the grip surface 76 can include a contoured protrusion extending from the top surface 77 of the slide cover 70. The grip surface 76 can also include a surface feature/texture on the top and/or side surfaces 77, 78 of the slide cover 70.

As outlined above, the slide cover 70 is slidably coupled to the housing 10 (top housing 20 and bottom housing 30). To provide a consistent profile along the control device 1, the side cover 70 can have a width and height corresponding to the width and height of the housing 1. As illustrated in FIGS. 1 and 2, the slide cover 70 can be received within the recessed surface 23 of the top housing 20 such that the width and height corresponds to the width and height of the housing 10. It is contemplated that the grip surface 76 of the slide cover 70 may extend above the width/height of the housing 10. However, in another example (not shown), the height/width of the grip surface of the slide cover 70 is less than the height/width of the housing 10.

During use of the control device 1, the control device 1 is first coupled to and positioned appropriately on the handpiece 110 of a surgical power tool 100. The surgeon may orient with control device 1 such that the bottom surface 33 of the housing 1 and the opening between arms 32 aligns with the handpiece 110. The control device 1 is then coupled to the handpiece 110 by a press-fit or snap-fit connection.

For example, the arms 32 of the housing 10 can flex/separate to advance over and around the handpiece 110. Depending on the surgical procedure, patient anatomy, and surgeon grip position and visibility, the surgeon may wish to position the control device 1 at various locations along and/or around the handpiece 110 of the power tool 100. Accordingly, once coupled to the handpiece 110, the position of the control device 1 can be adjusted along/around the handpiece 110 as desired by the surgeon. For example, the surgeon can slide the control device 1 forward or rearward along the handpiece 110. The surgeon can also rotate the control device 1 around the perimeter of the handpiece 110.

If desired, the surgeon can fix the location of the control device 1 by engaging a mechanical fastener/connection between the housing 10 and the handpiece 110. Alternatively/in addition, the surgeon can fix the position of the control device 1 with respect to the handpiece 110 by grasping the control device 1 and handpiece 110 around the periphery. The surgeon can then move the slide cover 70 to an operating position such that the input surface 51 of the input element 50 is exposed. To move the slide cover 70, the surgeon may provide pressure on the grip surface 76 in the direction of desired movement sufficient to overcome engagement features between the slide cover 70 and the top housing 10. In one example, lateral pressure may be applied to the protrusion extending from the top surface 77 of the slide cover 70. In another example, the surgeon may grasp the slide cover 76 at its side edges and pull/push the slide cover back, away from the input element 50.

With the control device 1 attached, the surgeon can then position the power tool 100 at its desired location at/in the surgical site to complete the medical procedure. Once positioned, the input element 50 can be activated by pressure applied by the surgeon's finger(s)/thumb at the input surface 51. In an example control device 1, depressing the input element 50 causes a carbon pill 55 overmolded into the input element 50 to complete an electrical connection with a corresponding contact 63 provided on the control unit 60. With the electrical connection in place, user input information is then transmitted to the power tool 100. By varying pressure on the input surface 51 the surgeon is able to vary the input information provided to the power tool 100. For example, increasing/decreasing the pressure provided on the input surface 51 can result in a corresponding increase/decrease in the speed, torque, etc. of the power tool 100. Once the medical procedure is complete (or the need for the power tool has ended), the surgeon can remove the power tool 100 from the surgical site. Before or after removing the power tool 100, the surgeon can reposition/close the slide cover 70 such that the slide cover 70 is positioned over the input surface 51. Closing the slide cover 70 is performed in a similar (but opposite) fashion as opening. The surgeon can provide pressure on the grip surface 76 in the direction of desired movement sufficient to overcome engagement between the engagement features between the slide cover 70 and the top housing 10. Once in the fully closed position, the recess 73 provided on the slide cover can engages the protrusion 25 provided in the top housing 10. By repositioning the slide cover 70 and engaging the protrusion 25, the surgeon prevents accidental activation of the power tool 100.

With the surgical tool 100 removed from the surgical site, the surgeon can then safely remove the control device 1 from the handpiece 110. If a mechanical fastener was used to fix the position on the handpiece 110 it must be disengaged. The surgeon can then slide/pull the control device 1 off of the handpiece 110. Once the control device is removed from the handpiece 110 it can be sterilized for reuse, recycled and/or disposed of Because the control device 1 can be separated from the handpiece 110 (upon completion of or during the surgical procedure), the control device 1 can be easily be cleaned and sterilized separate from the power tool 100.

Figure 12:
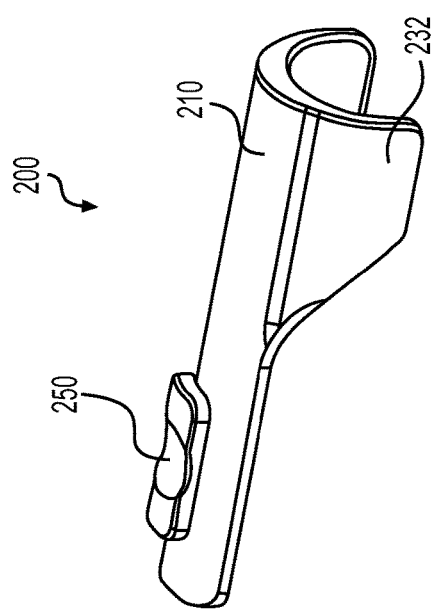
FIG. 12 is a perspective views of an example control device.

FIG. 12 provides another example control device 200. The control device 200 is similar to the control device 1 depicted in FIG. 1, like reference symbols are used to indicate like elements. The differences between the control device 200 and the control device 1 are discussed below. The control device 200 can include a sliding magnet 250 for providing input information to the control unit. As the magnet 250 is moved along the housing 210 is activates the contacts provided on the control unit. For example, the magnet 250 is moved between an on/off position along the housing 210, thereby providing on/off instructions to the power tool.

Figure 13:
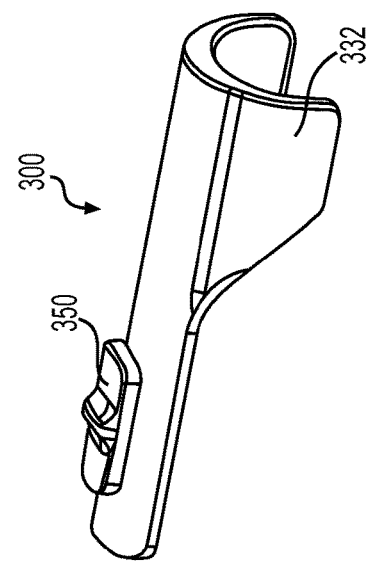
FIG. 13 is a perspective views of an example control device.

FIG. 13 provides another example control device 300. The control device 300 is similar to the control device 1 depicted in FIG. 1, like reference symbols are used to indicate like elements. The differences between the control device 300 and the control device 1 are discussed below. The control device 300 can also include a sliding magnet 350 for providing input information to the control unit. As the magnet 350 moves along the housing 310, the contacts on the control unit is activated. In the control device 300, the direction and/or location of the magnet 350 along the housing can be used vary the input information received at the control unit.

Figure 14:
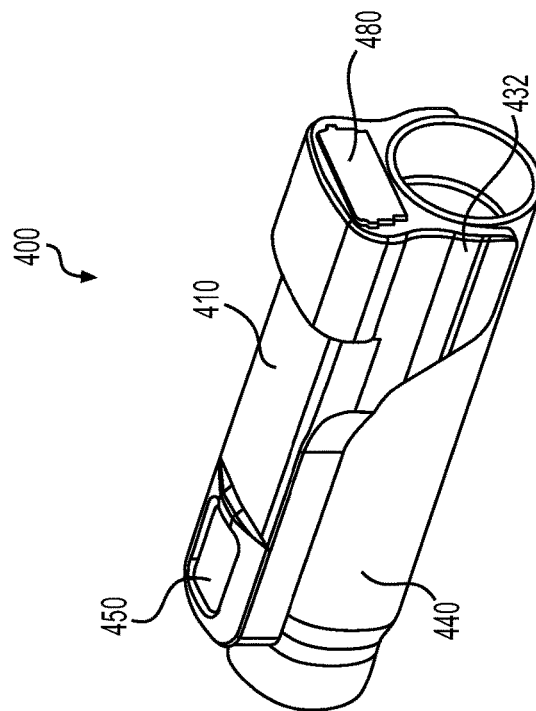
FIG. 14 is a perspective views of an example control device.

FIG. 14 provides another example control device 400. The control device 400 is similar to the control device 1 depicted in FIG. 1, like reference symbols are used to indicate like elements. The differences between the control device 400 and the control device 1 are discussed below. The control device 400 can include a popple/snap dome input element 450. Pressure provided at the input surface of the input element 450 completes the electrical connection between the input element 450 and contacts of the control unit. Releasing the pressure on the input surface disengages the electrical connection. As the popple/snap dome input element 450 is moved depressed/released a corresponding on/off instruction is sent to the power tool. In another example, the control device 400 includes a force sensor input element 450. As such, the varying the force/pressure applied at the input element 450 corresponds to a change in power tool operation. For example, as the pressure/force is increased the speed, torque, etc. of the power tool increases. The control device 400 can also include a replaceable and/or rechargeable battery 480. The battery 480 can be accessed via an opening provided at the proximal end of the control device 400.

Figure 15:
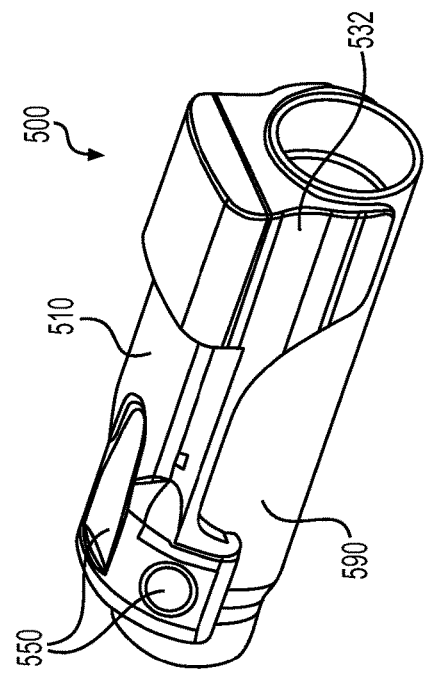
FIG. 15 is a perspective views of an example control device.

FIG. 15 provides another example control device 500. The control device 500 is similar to the control device 1 depicted in FIG. 1, like reference symbols are used to indicate like elements. The differences between the control device 500 and the control device 1 are discussed below. The control device 500 can include a capacitive touch sensor input element 550. The capacitive input element 550 can include multiple input surfaces capable of providing different input information to the power tool. For example, the various input surface can each provide separate instructions regarding speed, torque, illumination, irrigation, or any other function completed by the power tool.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. A control device for a surgical power tool comprising:
   a housing sized and configured to removably couple to a surgical power tool, the housing comprising a top housing coupled to a bottom housing;
   a control unit including a PCB (printed circuit board), the control unit located within the housing, wherein the control unit is configured to wirelessly transmits user input information received at an input surface to a surgical power tool;
   the input surface provided at the housing for receiving a user input, wherein the user input information varies in response to at least one of a pressure, a location, and a direction of the
   user input at the input surface, and further wherein the input surface including an anchor coupled to a bottom surface of the input surface and coupling the input surface to the housing, where the anchor extends from the bottom surface of the input surface and through openings provided in the control unit and PCB such that the input surface is coupled to the bottom housing; and
   a cover slidably coupled to the housing such that the cover is movable between a first position over at least a portion of the input surface, and a second position away from the input surface, the cover including a downwardly extending arm slidably engaged to at least one of a side surface and a bottom surface of the housing.

2. The device of claim 1,
   wherein the input surface is provided at the top housing and the bottom housing includes a mating surface extending in a direction opposite the input surface that is sized and configured to couple to a surgical power tool,
   wherein the housing includes a main body portion defined at the distal end of the housing, where the input surface and cover are provided on the main body portion of the housing,
   wherein the housing includes a base portion longitudinally spaced from and opposite the main body portion defined at the proximal end of the housing, the main body portion having a width less than the base portion and a length longer than the base portion,
   wherein a thickness of the main body portion of the housing is less than a thickness of the base body portion of the housing to improve visibility between the proximal end of the housing and a distal end of the surgical power tool.

3. The device of claim 2, wherein the top housing is integrally formed with the bottom housing.

4. The device of claim 1, further comprising arms extending from the housing, the arms sized and configured to engage a portion of an outer perimeter of a power tool, the arms extending from opposing sides of the housing in a direction away from the bottom surface of the housing and include an inner surface having a shape corresponding to an outer perimeter of a power tool.

5. The device of claim 4, wherein the arms are sized and configured to couple the control device to a handpiece of a power tool, the arms extending around a majority of a perimeter of the handpiece when the control device is coupled to the handpiece.

6. The device of claim 4, wherein the arms couple the housing to a power tool by at least one of a snap fit, press fit, a mechanical fastener, a weld and an adhesive.

7. The device of claim 1, wherein the input surface is accessible via an opening in a top surface of the housing, input surface extending at least partially into the opening on the housing.

8. The device of claim 1, wherein the input surface is composed of a pressure responsive material,
   wherein the input surface is located proximate the control unit such that a user input at the input surface activates the control unit.

9. The device of claim 1, wherein the input surface is integrally formed with the housing.

10. The device of claim 1, wherein the control unit includes a battery.

11. The device of claim 1, wherein the housing is movable along a handpiece of a surgical power tool.

12. The device of claim 1, wherein the control unit is configured to receives operation information from a surgical power tool.

13. The device of claim 1, wherein the cover is slidably coupled within a recess provided on a top surface of the housing such that a width and a height of the cover corresponds to a width and height of the housing,
   wherein the bottom surface of the housing includes a recessed groove for receiving the arm of the cover, proximal and distal ends of the groove defining the first position and the second position of the cover,
   wherein the bottom surface of the cover includes an elongated channel slidably engaging a corresponding protrusion extending from the top surface of the housing, engagement between the channel and the protrusion guiding movement of the cover along the housing.

14. A surgical tool and control device comprising: a surgical power tool;
   a control device removably coupled to the surgical power tool, the control device including:
   a housing comprising a top housing coupled to a bottom housing, the bottom housing including arms for coupling the control device to the power tool, the arms extending from the bottom housing and engaging at least a portion of the outer perimeter of a handpiece of the power tool;

a control unit configured to wirelessly transmits user input information received at a pressure responsive touch pad to the power tool for directing a speed of the power tool, the control unit including a PCB (printed circuit board);
the pressure responsive touch pad located on a top surface of the control device for receiving a user input, the touch pad including an anchor coupled to a bottom surface of the touch pad and coupling the touch pad to the housing, the anchor extending from the bottom surface of the touch pad and through openings provided in a control unit and the PCB to fixedly couple the pressure responsive touch pad to the bottom housing;
a cover slidably coupled to the housing and movable between a first position over the touch pad such that the touch pad cannot receive a user input, and a second position away from the touch pad, the cover including downwardly extending arms slidably engaged to at least one of side surfaces and a bottom surface of the housing;
wherein, when coupled to the surgical power tool, the control device is movable along a length and around a circumference of the handpiece of the surgical power tool as desired by an operator to adjust a location of the control device with respect to a distal end of the surgical power tool.

15. The surgical tool and control device of claim 14, wherein the control unit includes a battery,
wherein the user input information is received by a control unit of the power tool and the speed of the power tool varies in response to a pressure of the user input received at the touch pad,
wherein the user input information is transmitted to the control unit of the power tool independent of the location of the control device on the handpiece of the power tool.

16. A method of controlling a surgical power tool using the control device recited in claim 1, the control device movably and releasably coupled to the power tool, the method comprising:
coupling the control device to a handpiece of a surgical power tool such that the control device is movable along a length and around a circumference of the handpiece,
moving the control device to a desired position on the handpiece of the surgical power tool to adjust a location of the control device with respect to a distal end of the surgical power tool,
moving the cover slidably coupled to the control device to a second position away from the input surface provided on the control device, the cover including downwardly extending arms slidably engaged to at least one of the side surface and the bottom surface of the control device;
activating the power tool by providing a user input at the input surface provided on the control device,
transmitting via wireless transmission an operation signal from the control device to the power tool corresponding to the user input,
operating the power tool according to the operation signal, and
moving the cover to a first position over the input surface to prevent user input and accidental activation of the surgical power tool.

17. The method of claim 16, wherein coupling the control device to the surgical power tool includes:
aligning the control device over the power tool such that an opening provided between arms extending from a bottom surface of the control device is positioned over the handpiece, pressing the control device onto the handpiece such that the arms expand to advance the control device onto the handpiece, where the arms advance over and around the handpiece.

18. The method of claim 16, wherein moving the control device into the desired position includes at least one of sliding the control device along the length of the handpiece and rotating the control device around the circumference of handpiece to the desired position in response to at least one of a type of surgical procedure being performed, a desired visibility of a surgical site, patient anatomy, and user anatomy.

19. The method of claim 16, further including:
varying the user input provided at the input surface,
transmitting a varied operation signal from the control device to the power tool corresponding to the varied user input, and
operating the power tool according to the varied operation signal,
wherein providing a user input and a varied user input includes applying a pressure at an input surface provided on the control device.

20. The device of claim 1, wherein, when coupled to a surgical power tool, the housing is movable along a length and around a circumference of a surgical power tool as desired by an operator to adjust a location of the control device with respect to a distal end of a surgical power tool.

* * * * *